(12) United States Patent
Jomaa et al.

(10) Patent No.: US 7,875,279 B2
(45) Date of Patent: Jan. 25, 2011

(54) INACTIVATION OF GENES OF THE MEP PATHWAY

(75) Inventors: Hassan Jomaa, Giessen (DE); Matthias Eberl, Giessen (DE); Boran Altincicek, Fernwald-Annerod (DE)

(73) Assignee: Bioagency AG, Hamburg (DE)

( * ) Notice: Subject to any disclaimer, the term of this patent is extended or adjusted under 35 U.S.C. 154(b) by 1552 days.

(21) Appl. No.: 10/475,510

(22) PCT Filed: Apr. 13, 2002

(86) PCT No.: PCT/EP02/04134
§ 371 (c)(1), (2), (4) Date: Jan. 29, 2007

(87) PCT Pub. No.: WO02/095011
PCT Pub. Date: Nov. 28, 2002

(65) Prior Publication Data
US 2008/0206267 A1    Aug. 28, 2008

(30) Foreign Application Priority Data
Apr. 23, 2001  (DE) .................................. 101 19 905

(51) Int. Cl.
A61K 39/395    (2006.01)
A61K 51/00    (2006.01)
A01N 63/00    (2006.01)
C12P 21/00    (2006.01)

(52) U.S. Cl. ................. 424/154.1; 424/130.1; 424/1.11; 424/93.4; 435/69.1

(58) Field of Classification Search ...................... None
See application file for complete search history.

(56) References Cited
FOREIGN PATENT DOCUMENTS

| WO | WO 99/53071 | 10/1999 |
| WO | WO 99/58649 | 11/1999 |
| WO | WO 00/72022 | 11/2000 |

OTHER PUBLICATIONS

Gustafson, C.E. et al. "Identification of the *Escherichia coli* lytB Gene, Which Is Involved in Penicillin Tolerance and Control of the Stringent Response" *Journal of Bacteriology*, Feb. 1993, pp. 1203-1205, vol. 175, No. 4.

Bouvier, J. et al. "Nucleotide sequence of the *lsp-dapB* interval in *Escherichia coli*" *Nucleic Acids Research*, Oct. 31, 1990, vol. 19, No. 1.

Cunningham, F. et al., "Evidence of a Role for LytB in the Nonmevalonate Pathway of Isoprenoid Biosynthesis", pp. 5841-5848, *Journal of Bacteriology*, Oct. 2000, vol. 182, No. 20.

Altincicek B. et al., "Cutty Edge: Human gamma/delta T cells are Activated by Intermediates of the 2-C-Methyl-D-Erythritol 4-Phosphate Pathway of Isoprenoid Biosynthesis", *Journal of Immunology*, Bd. 1666, Nr. 6, Mar. 2001, pp. 3655-3658.

Belmant C. et al., "3-Formyl-1-Butyl pyrophosphate: A Novel Mycobacterial Metabolite-Activating Human gamma-delta T Cells", *The Journal of Biological Chemistry*, Bd. 274, Nr. 45, Nov. 1999, pp. 23079-32084.

Jomaa, H. et al., "Vgamma9/Vdelta2 T Cell Activation Induced by Bacterial Low Molecular Mass Compounds Depends on the 1-Deoxy-D-Xylulose 5-Phosphate Pathway of Isoprenoid Biosynthesis", *FEMS Immunology and Medical Microbiology*, Bd. 25, 1999, pp. 371-378.

Hintz M. et al., "Indentification (E)-4-Hydroxy-3-Methyl-But-2-Enyl Pyrophosphate as a Major Activator For Human gammadelta T Cells in *Escherichia coli*", *FEBS Letters*, Elsevier Science Publishers, Amesterdam, NL, Bd. 509, Nr. 2, Dec. 2001, pp. 317-322.

Feurle J. et al., "*Escherichia coli* Produces Phosphoantigens Acticated Human gammadelta T Cells", *Journal of Biological Chemistry*, Bd. Nr. 1, Jan. 4, 2002, pp. 148-154.

Seemann M. et al., "Isoprenoid Biosynthesis Via the Methylerthritol Phosphate Pathway: Accumulation of 2-C-Methyl-d-Erythritol 2,4-Cyclodiphosphate in a gcpE Deficient Mutant of *Escherichia coli*", *Tetrahedron Letters*, Elsevier Science Publishers, Amsterdam, NL, Bd. 43, Nr. 5, Jan. 28, 2002, pp. 775-778.

*Primary Examiner*—Vanessa L Ford
*Assistant Examiner*—Lakia J Tongue
(74) *Attorney, Agent, or Firm*—Saliwanchik, Lloyd & Saliwanchik (57) ABSTRACT

The invention relates to cells and organisms as well as to methods for producing said cells and organisms, according to which intermediates of the mevalonate-independent pathway for isoprenoid biosynthesis (MEP pathway) are enriched by deleting or inactivating genes. The derivatives can also be enriched by using enzyme inhibitors. The enriched intermediates may be used as substrates in enzyme activity tests. The inventive cells and organisms and the enriched intermediates can further be used in the production of medicaments.

3 Claims, 2 Drawing Sheets

INACTIVATION OF GENES OF THE MEP PATHWAY

CROSS-REFERENCE TO RELATED APPLICATION

This application is the U.S. national stage application of International Patent Application No. PCT/EP02/04134, filed Apr. 13, 2002.

BACKGROUND OF THE INVENTION

This invention refers to cells and organisms for which intermediates of the mevalonate independent isoprenoid metabolism pathway (MEP pathway) are enriched through deletion or inactivation of genes. Furthermore, it refers to processes for producing intermediates and products derived from the MEP pathway from organisms, for which the genes according to the invention have been deleted or inactivated and genetic engineering and convention processes for producing these organisms. It also refers to the application of enzyme inhibitors for enriching MEP pathway intermediates. It also refers to the therapeutic application of cells and organisms for which the genes or enzymes according to the invention have been deleted or inhibited and the production of medication from these cells and organisms.

The biosynthesis of isoprenoids using the classic acetate/mevalonate pathway (Beytia E D, Porter J W, *Annu Rev Biochem,* 1976; 45: 113-42) and an alternative, mevalonate independent biosynthesis pathway, the 2-methyl-D-erythritol pathway (MEP pathway, synonymous with DOXP pathway) is known (Rohmer M. *Nat Prod Rep,* 1999 October; 16(5): 565-74). Both pathways lead to isopentenylpyrophosphate (IPP), the common precursor of all higher isoprenoids. While the acetate/mevalonate pathway has been known for some time and is fully understood, at present not all biosynthetic steps in the reaction of the MEP pathway are known.

In the past, various biotechnological processes have been derived, based on the application of knowledge regarding the MEP pathway:

1. Inhibitors of various enzymes through the MEP pathway are suitable as disinfectants and herbicides as the MEP pathway does not occur in humans.

2. Certain intermediates of the MEP pathway lead to a massive stimulation of human gamma/delta T cells. These intermediates are suitable as immunomodular medicines.

3. Through the over-expression of certain genes of the MEP pathway (e.g. DOXP synthase, LytB), the enriching of higher isoprenes can be achieved as subsequent products of the MEP pathway.

It was previously unknown that through the deletion of a gene of the MEP pathway or through inactivation of the corresponding enzyme, an intermediate of the MEP pathway can be achieved.

It is known that human gamma/delta T cells are activated through one or more intermediate of the MEP pathway. This means that with the incubation of peripheral blood lymphocytes with extracts from organisms which have an MEP pathway, there is a selective proliferation and cytokine secretion of the gamma/delta T cell population (Jomaa H, Feurle J, Luhs K, Kunzmann V, Tony H P, Herderich M, Wilhelm m, *FEMS Immunol Med. Microbiol.* 1999 September; 25(4): 371-8). The exact chemical composition of this activating substance of substances is still unknown. Published data suggest that 3-formyl-1-butylpyrophosphate plays a role as a hypothetical intermediate of the MEP pathway in activating gamma/delta T cells (Belmant C, Espinosa E, Poupot R, Peyrat M A, Guiraud M Poquet Y, Bonneville M Fournte J J, J. Biol. Chem. 1999 Nov. 5; 274(45): 32079-84).

Figure 1:
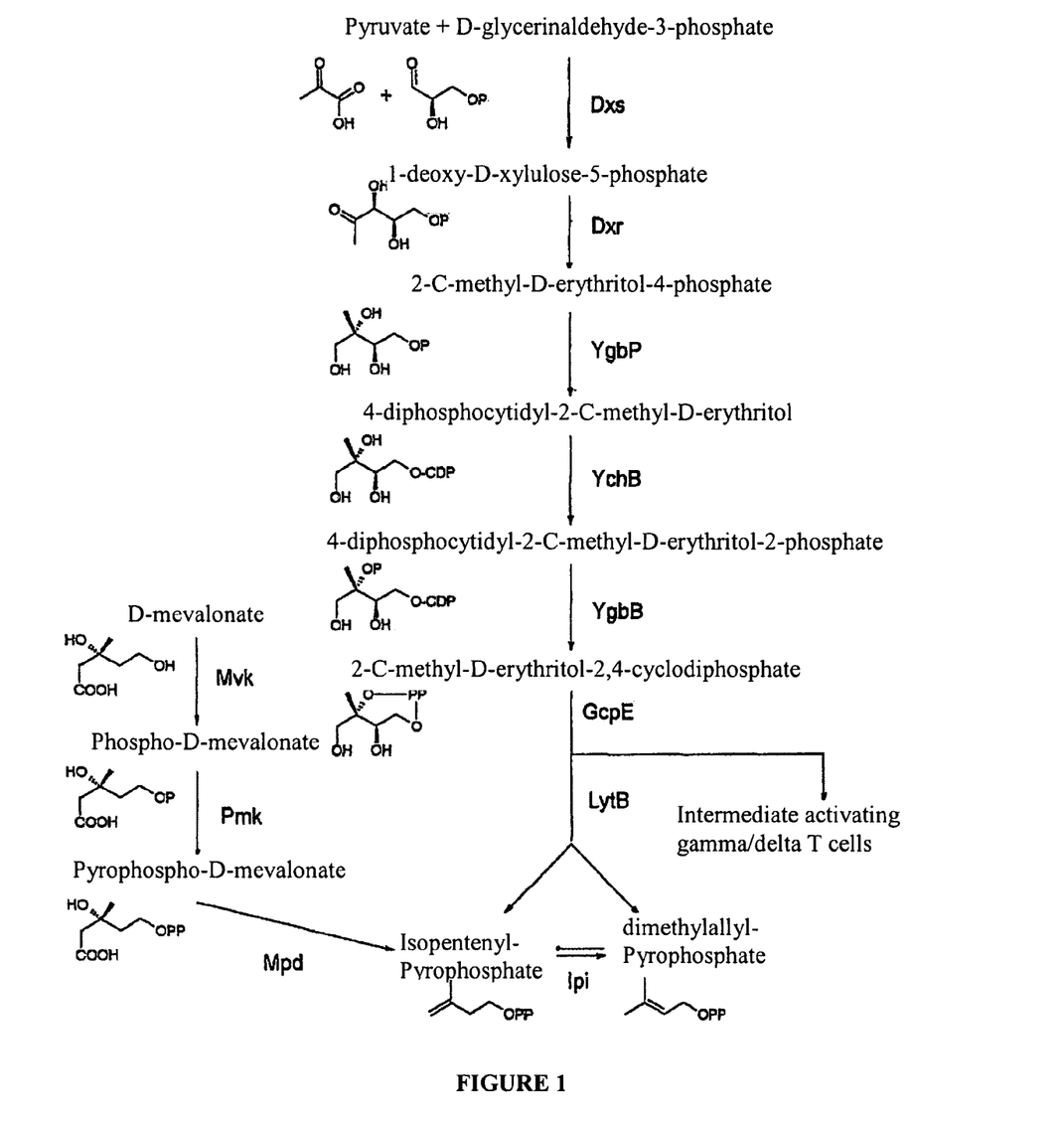
FIG. 1 shows the principle of enriching the intermediates of the MEP pathway through the deletion of genes of the MEP pathway. Substantial steps of the MEP pathway occurring naturally in *E. coli* are represented with the enzymes Dxs, Dxr, YgbP, YchB, YgbB, Gcpe, LytB. In order to be able to delete genes of the MEP pathway, genes of the mevalonate pathway (coding for Mvk, Pmk, Mpd) are introduced through genetic engineering. Through the deletion of lytB, the intermediates are enriched which activate the gamma/delta T cells.

Consequently, it was shown that bacteria, where various genes of the MEP pathway (e.g. DOXP reductoismerase, gepE) had been deleted, were no longer able to activate gamma/delta T cells (Altincicek B, Moll J, Campos N, Foerster G, Beck E, Hoeffler J F, Grosdemange-Billiard C, Rodriguez-Concepcion M, Rohmer M, Boronat A, Eberl M Jomaa H, *J. Immunol.* 2001 Mar. 15; 166(6):3655-8). In order to produce these deletion mutations it is necessary to introduce genes of the mevalonate pathway using genetic engineering into the bacteria. As a result, the bacteria can then survive in the medium in the presence of mevalonate if the MEP pathway is no longer functional (FIG. 1).

BRIEF SUMMARY OF THE INVENTION

The invention relates to cells and organisms as well as to methods for producing said cells and organisms, according to which intermediates of the mevalonate-independent pathway for isoprenoid biosynthesis (MEP pathway) are enriched by deleting or inactivating genes. The derivatives can also be enriched by using enzyme inhibitors. The enriched intermediates may be used as substrates in enzyme activity tests. The inventive cells and organisms and the enriched intermediates can further be used in the production of medicaments.

BRIEF DESCRIPTION OF THE DRAWINGS

The following explains the invention using the enclosed figures.

DETAILED DISCLOSURE OF THE INVENTION

Figure 2:
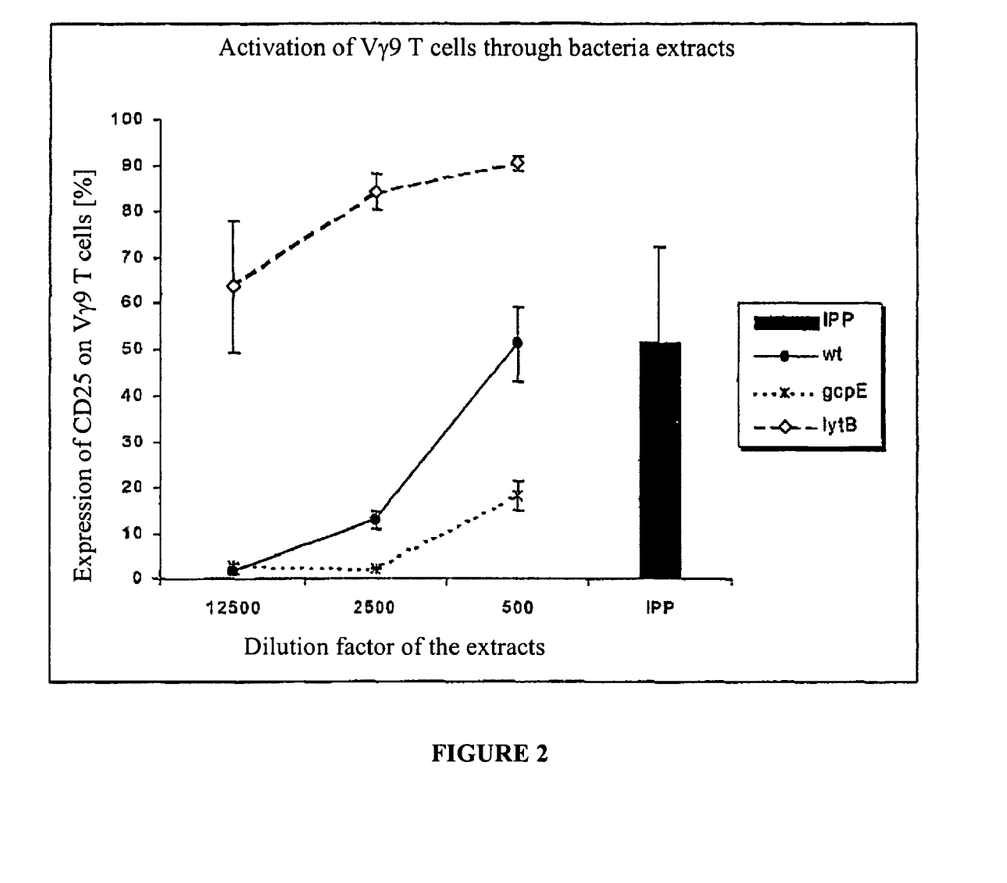
FIG. 2 shows the activation of gamma/delta T cells from the blood of healthy donors, measured as an expression of CD25, through extracts from various bacteria sources (wild type, wtDeltagcpE, wtDeltalytB) in various dilution stages. IPP serves as a control with an end concentration of 10 uM (IPP activates gamma/delta T cells substantially weaker than the intermediate according to the invention, but is suitable as a control for the test system). The wtDeltagcpE mutants were produced analogously to the wtDeltagcpB mutants.

Surprisingly, it was found that bacteria, whose lytB gene had been deleted (example 1) activated gamma/delta T cells significantly more strongly than typical bacteria (example 2, FIG. 2). An essential participation of the lytB gene in the MEP pathway was displayed (example 3). A blockage of the MEP pathway at the level of the lytB enzyme thus leads to the intermediate, which is responsible for the gamma/delta T cells, being enriched.

Therefore, a process is available, through which the enriching of intermediates of the MEP pathway is achieved through deletion, mutation or functional inactivation of the corresponding genes. The enriching of the intermediates of the MEP pathway can also be achieved through inhibiting the enzymatic function of the corresponding polypeptide.

DNA sequences, which code for a polypeptide with the amino acids represented in SEQ ID NO: 2 or for an analogue or derivative of the polypeptide according to SEQ ID NO: 2, are particularly suitable for carrying out the process according to the process, where one or more amino acids are deleted, added or substituted by other amino acids without the enzymatic effect of the polypeptide being substantially reduced.

Furthermore, the invention is defined by claims 1-17. Further images of the invention are defined in the subordinate claims.

The genes and their genetic products (polypeptide) are listed in the sequence protocol with their primary structures and are allocated as follows:

SEQ ID NO: 1 lytB-gene
SEQ ID NO:2 lytB-protein.
The sequences come from *escherichia coli*.

Apart from the DNA sequences named in the sequence protocol, others are suitable which have another DNA code as a result of the degeneration of the genetic code but which code for the same polypeptide or for an analogue or derivative of the polypeptide. This also includes sequences which come from organisms other than *E. coli*, specifically, other bacteria, algae, plants and protozoa, and which are recognized, based on sequence comparisons or function analyses, as homologous to the sequences named in the sequence protocol.

The invention refers to cells and organisms and the production of cells and organisms, for which the genes according to the invention are functionally inactivated principally as a result of known methods. The genes do not have to be fully inactivated but instead can have their function reduced or modified. This can be achieved by the following:

Complete or partial deletion of the genes
Substitution of the gene through an artificial DNA sequence or a gene for a selection marker
Insertion of a gene for a selection marker
Deletion, insertion and substitution of one or several base pair
Mutations in the 5' and 3' area of the coding sequences (influence of promoter, enhancer, terminator sequences, ribosome conjugates)
Introduction of DNA constructs which code for antisense DNA
Application of mutagen agents, ionising radiation, UV radiation
Screening for spontaneous mutants.

The inactivation or modification of the sequences according to the invention can occur in bacteria, algae, plants and protozoa. In order to maintain stable mutants, it can be necessary to introduce the genes of the acetate/mevalonate pathway partially or in full and, if necessary, to add mevalonate or another intermediate of the MEP pathway to the medium. Alternatively or additionally, intermediates of the MEP pathway or derivatives or analogues to these intermediates (e.g. 3-methyl-3-buten-1-ol, 3-methyl-2-buten-1-ol) can be added to the medium.

Cells and organisms can also be used, which do not naturally have the MEP pathway, if genes of the MEP pathway have been introduced through genetic engineering and bioengineering methods. It is also possible to achieve enriching of intermediates of the MEP pathway of their derivatives by only incompletely introducing the genes of the MEP pathway. Mammal and insect cells, lower and higher fungi, slime mold and various protozoa, among others, are suitable for this.

Apart from through genetic methods, inactivation or reduction of the enzymatic activity of the polypeptides according to the invention can also be achieved through enzyme inhibitors which are added to the culture medium of the organisms or cell extracts from the organisms. The enzyme inhibitors can have synthetic or natural conjugates which reversibly or irreversibly inhibit the function of the polypeptide through competitive or allosteric interactions.

The cells and organisms according to the invention, including complete plants and parts of plants, can be reproduced and cultivated through known processes. A co-culture with other cells or organisms, including those which do not have an MEP pathway, is also possible. The enriched intermediates of the MEP pathway or their derivatives can be obtained through breaking down the cells or from the culture. Various known methods are suitable for purifying the intermediates, including chromatography, electrophoreses and precipitation (e.g. as barium salts).

The enriched intermediates of the MEP pathway are suitable for various applications. It has been found that the intermediates contain the product of the GcpE enzyme and the substrate of the LytB enzyme. Thus, the intermediates can be used as substrates in the enzyme activity test for LytB and GcpE. In the activity test for GcpE, the reverse reaction is observed. This type of enzyme activity test is suitable for finding GcpE and LytB inhibitors.

The enriched intermediates of the MEP pathway are also suitable for producing medicines. The effectiveness of the substances is based on the activation of gamma/delta T cells. Depending on the area of application, the immunity can be strengthened (e.g. against tumors) or immunological tolerance against auto-antigens and allergens can be induced.

Areas of application are the treatment of immune, autoimmune diseases and allergies. For example: allergies, multiple sclerosis, rheumatoid arthritis, Hashimoto's thyroiditis, myasthenia gravis, lupus erythematosus, diabetes mellitus, primary biliary cirrhosis, active chronic hepatitis, adrenalitis/Addison's disease, polymyositis, dermatomyositis, auto-immune haemolytic anaemia, myocardial and cardiac infections, scleroderma, uveitis (phacouveitis, sympathetic ophthalmia), pemphigus vulgaris, pemphigoid, pernicious anaemia, auto-immune atrophic gastritis, inflammatory disease of the intestines such as Crohn's disease and colitis ulcerosa, inflammatory disease of the lungs such as asthmatic diseases and bronchitis.

The application is preferred for morbus Crohn, colitis ulcerosa, multiple sclerosis, asthma, chronic bronchitis, allergies.

Other applications are infections of the bone, especially osteoporosis.

The intermediates of the MEP pathway can be isolated from the organisms according to the invention or used as raw extracts for medical application. The complete organisms can also be used living or dead. The intermediates and organisms according to the invention can be used alone or in combination with other medications. Application as adjuvant for strengthening or for modulation of an immune response is also included. Preferred methods of application are oral, inhalative and rectal application, as well as application on the skin or mucous membranes.

The following are suitable as pharmaceutical compositions: tablets, drops, capsules, pills, granules, suppositories, solutions, suspensions and emulsions, pastes, ointments, gels, creams, lotions, powders and sprays.

Tablets, drops, capsules, pills and granules can contain the active ingredients alongside the usual carriers such as (a) fillers and mixers, e.g. starch, lactose, cane sugar, glucose, mannitol and silicic acid, (b) binders, e.g. carboxymethylcelulose, alginate, gelatine, polyvinylpyrrolidone, (c) moisturizers, e.g. glycerine, (d) explosive, e.g. agar-agar, calcium carbonate and sodium carbonate, (e) emulsifier, e.g. paraffin (f) re-absorption accelerator, e.g. quanternary ammonium conjugates, (g) nets, e.g. cetylalcohol, glycerine monostearate, (h) absorbers, e.g. kaolin and bentonite and (i) lubricant, e.g. talcum, calcium and magnesium stearate and solid polyethylglycol or mixtures of the substances listed in (a) to (i). Moreover, the conjugates according to the invention can be included in other carriers such as plastics (plastic chains for local treatment), collages or bone cement.

Tablets, drops, capsules, pills and granules can be produced with the usual, if necessary opaque, casings and cases and also combined such that the active ingredients are only released, or preferably with a delay, in a specific section of the intestinal tract where embedders can be used, e.g. polymer substances and waxes.

The active ingredients can also exist in micro-capsule form in one or more of the above carriers.

Suppositories can contain the usual water soluble or insoluble carriers along with the active ingredients, e.g. polyethylglycol, fats, e.g. cocoa fat and higher ester (e.g. C14 alcohol with C16 fatty acid) or mixtures of same.

Ointments, pastes, creams and gels can contain the usual carriers along with the active ingredients, e.g. animal and vegetable fats, waxes, paraffin, starch, tragant, cellulose derivatives, polyethylglycol, silicone, bentonite, silicic acid, talcum and zinc oxide or mixtures of same.

Powders and sprays can contain the usual carriers along with the active ingredients, e.g. lactose, talcum, silicic acid, aluminium hydroxide, calcium silicate and polyamide powder or mixtures of same. In addition, sprays can contain propellants such as CFCs.

Solutions and emulsions can contain the usual carriers along with the active ingredients, such as solvents, solubilisers and emulsifiers, e.g. water, ethylalcohol, isopropylalcohol, ethylcarbonate, ethylacetate, benzylalcohol, benzylbenzoate, propylenglycol, 1,3-butylenglycol, dimethylformamide, oils, especially cotton seed oil, peanut oil, maize oil, olive oil, *ricinus* oil and sesame oil, glycerine, glycerine formal, tetrahydrofurylalcohol, polyethylglycols and fatty acid ester of sorbitol or mixtures of same.

Particularly beneficial is the selection of a medical application which also contains a substance which can be recognized by the immune system as a foreign object or autoantigen.

Example 1

Construction of lytB Deletion Mutant

Construction of the Gene Exchange Plasmid pKO3-ΔlytB

In order to produce a lytB deletion mutant from *E. coli*, the pKO3 vector was used (Link, A. J.; Philips, D.; Church, G. M.; J. Bacteriol 179, 6228-6237). In order to produce the deletion design, two sequences were amplified downstream and upstream of the lytB gene in two asymmetrical PCR stages. The primers were used in a 1:10 molar ratio (50 nM and 500 nM). Both PCR products were fused in a second PCR amplification to form one product. The product was cloned using the pCR-TA-TOPO cloning kit (Invitrogen) and recloned using the restriction interfaces Bam HI and Sal I in the pKO3 vector. The following primers were used:

(SEQ ID NO: 3)
lytB-N-out,
5'-TAGGATCCccggcctagatgactgcg-3';

(SEQ ID NO: 4)
ltyB-N-in,
5'-CCCATCCACTAAACTTAAACAcaacaggatctgcatgttacg-3';

(SEQ ID NO: 5)
ltyB-C-in,
5'-TGTTTAAGTTTAGTGGATGGGcgtgaagtcgattagtcat-3';

(SEQ ID NO: 6)
ltyB-C-out,
5'-TA<u>GTCGAC</u>agaaccacccatgatcacc-3'.

The restriction interfaces are underlined. Overlapping sequences, which define a 21 bp-"in frame" insertion, are printed in bold.

Construction of the Synthetic Mevalonate Operon pSC-MVA

In order to be able to produce mutants whose individual genes of the MEP pathway are deleted, first of all a genetically altered *E. coli* source was produced which was able to use mevalonate from the culture medium for the synthesis of IPP. To do this, a synthetic operon was constructed which contained the gene for the following enzyme of the mevalonate pathway from *saccharomyces cerevisiae* (yeast): mevalonate kinase (ERG12), phosphomevalonate kinase (ERG8) and diphosphomevalonate-decarboxylase (ERG19). The three genes were amplified in three asymmetrical PCR stages with genome yeast DNA as a matrix, with the primers being used in a 1:10 molar ratio (50 nM and 500 nM). Ribosome binders were included with the primers. The three PCR products were mixed so that they could hybridize with the overlapping areas and were amplified using the external primer as a fragment. The product was cloned in the pBAD vector using pBAD-TA-TOPO cloning kits (Invitrogen) and verified using restriction and sequence analysis. The following primer set was used:

(SEQ ID NO: 7)
Mev-kin-Sc-for:
5'-T*AGGAGG*AATTAACCATGTCATTACCGTTCTTAACT-3'

(SEQ ID NO: 8)
Mev-kin-Sc-rev:
5'-TTGATCTG*CCTCCT*ATGAAGTCCATGGTAAATT-3'

(SEQ ID NO: 9)
Pmev-kin-Sc-for:
5'-ACTTCAT*AGGAGG*CAGATCAAATGTCAGAGTTGAGAGCCTTC-3'

(SEQ ID NO: 10)
Pmev-kin-Sc-rev:
5'-GAGTATTAT*CCTCCT*ATTTATCAAGATAAGTTTC-3';

(SEQ ID NO: 11)
Decarb-Sc-for:
5'-GATAAAT*AGGAGG*TAATACTCATGACCCGTTACACAGCATCC-3'

(SEQ ID NO: 12)
Decarb-Sc-rev:
5'-TTATTCCTTTGGTAGACCAGT-3'.

Overlapping sequences are printed in bold and sequences which define ribosome conjugates are in italics.

In order to check the functionality of the operon, the sensitivity to fosmidomycin from bacteria which have been transformed with the synthetic operon was tested in the presence of mevalonate. As expected, bacteria grew, which contained fosmidomycin at a reduced rate as long as the medium contained mevalonate. Without mevalonate, the bacteria died under fosmidomycin.

Construction of the Deletion Mutant wtΔlytB

The plasmid pKO3-DeltalytB was transformed in the *E. coli* K-12 source DSM No. 498 (ATCC 23716), which had previously been transformed with pSC-MVA. The medium was supplemented with 100 uM mevalonate. After 1 hour incubation at 30° C., bacteria with integrated plasmid were selected through a temperature shift to 43° C. As a result of the subsequent test for sucrose resistance and chloramphenicol sensitivity, the bacteria, which had lost the vector sequences, were selected and then analyzed through PCR for the desired gene type.

Example 2

Activation of Gamma/Delta T Cells Through Enriched Intermediates of the MEP Pathway The enriching of intermediates of the MEP pathway was detected from the ability of these intermediates to activate gamma/delta T cells. Various bacteria sources (wild type, wtDeltagcpE, wtDeltalytB) were cultivated in liquid cultures up an optical thickness of approximately 0.8. Obtaining low molecular extracts (low molecular weight, LMW) with an exclusion limit of 3 kDa occurs as described (Jomaa H, Feurle J, Luhs K, Kunzmann V, Tony H P, Herderich M and Wilhelm M, *FEMS Immunol Med Microbiol*, 25:371). Lymphocytes are obtained from the peripheral blood of three healthy donors through the ficoll-density gradient centrifugation. For each test, 2 lots of $10^5$ of the cells obtained are shown in a volume of 0.2 ml RPMI-1640-Medium (Life Technologies), which was enriched with 25 mM HEPES, 2 mM L-glutamine, 0.025 mg/ml gentamycin, 100 U/ml human interleukin-2 (IL-2) (all from Life Technologies), and 10% human AB serum (Bavarian Red Cross). LMW preparations were added to various solutions, IPP (sigma) was used in a final concentration of 10 uM as a positive control. The incubation was carried out at 37° C. and 5% $CO_2$ in the incubator. After 72 hours, the cells were harvested and analyzed in a throughflow cytometer. The expression of the activation marker CD25 was measured on the surface of V gamma $9^+$ T cells using the monoclonal antibodies CD25-PE (B1.49.9), V gamma 9-FITC (Immu360) and CD3-PC5 (UCHT1) from the Beckman-Coulter Company. Extracts from the wild type bacteria source activated the gamma/delta T cells at a concentration of 1:500 (corresponds to approx. $2\times10^7$ bacteria/10. Extracts from the DeltagcpE-deletion mutants led to a significantly reduced activation. By contrast, the activation by extracts from the DeltalytB-deletion mutants was considerably stronger than through extracts from the wild type source. A significant gamma/delta T cell activation was also measured at a concentration of 1:12500 (corresponds to approx. $8\times10^5$ bacteria/ml) (FIG. 2).

Example 3

Participation of lytB in the MEP Pathway

All lytB deletion mutants obtained grew strictly mevalonate dependent. In order to investigate this observation more closely, the deletion mutants wtDeltalytB were complemented by a wild type lytB gene on a plasmid. The lytB gene was amplified with the primer eclytbfor (5'-GGATCCATG-CAGATCCTGTTGGCCAAC-3', SEQ ID NO: 13) and eclty-brev (5'-AAGCTTTTAATCGACTTCACGAATATCG-3', SEQ ID NO: 14) from genomic *E. coli* DNA and cloned in the pCR2.1-TOPO vector. The insert was recloned through the restriction interfaces BamHI and HindIII and in the expression vector pQE30. Bacteria from the wtDeltalytB source, which were transformed with this construct, were able to grow without mevalonate. This result confirms that lytB is an essential participant in the MEP metabolism pathway. The enriched intermediates therefore come from the MEP pathway.

The invention claimed is:

1. A method of activating γδ (gamma delta) T-cells in a subject comprising administering a composition comprising an intermediate of the melavonate independent isoprenoid metabolism pathway (MEP) to a subject in an amount effective to activate γδ T-cells in said subject, wherein the intermediate of the MEP pathway is 3-formyl-1-butylpyrophosphate obtained by a process comprising: deleting lytB in selected cells or organisms to reduce the enzymatic activity of a gene product encoded by lytB within the MEP pathway and producing an accumulation of said intermediate of the MEP pathway within the selected cell or organism is from bacteria.

2. The method according to claim 1, wherein the process further comprises concentrating said intermediate of the MEP pathway.

3. The method according to claim 1 wherein the method additionally comprises administering an immunogen to the subject.

* * * * *

UNITED STATES PATENT AND TRADEMARK OFFICE
CERTIFICATE OF CORRECTION

PATENT NO. : 7,875,279 B2  
APPLICATION NO. : 10/475510  
DATED : January 25, 2011  
INVENTOR(S) : Hassan Jomaa, Matthias Eberl and Boran Altincicek It is certified that error appears in the above-identified patent and that said Letters Patent is hereby corrected as shown below:

Column 1,  
Line 20, "convention processes" should read --conventional processes--.  
Line 56, "one or more intermediate" should read --one or more intermediates--.  
Line 61, "Wilhelm m," should read --Wilhelm M,--.  
Line 64, "substance of substances" should read --substance or substances--.

Column 2,  
Line 1, "Guiraud M Poquet Y, Bonneville M Fournte" should read  
   --Guiraud M, Poquet Y, Bonneville M, Fournte--.

Column 3,  
Line 16, "escherichia coli" should read --Eschericia coli--.  
Lines 36-37, "base pair" should read --base pairs--.

Column 4,  
Lines 63-64, "carboxymethylcelulose" should read --carboxymethylcellulose--.

Column 7,  
Line 22, "up an optical" should read --up to an optical--.  
Line 35, "(sigma)" should read --(Sigma)--.

Column 8,  
Line 9, "bacteria/10)" should read --bacteria/ml)--.

Column 15,  
Line 39, "melavonate" should read --mevalonate--.

Signed and Sealed this  
Twelfth Day of April, 2011

David J. Kappos  
*Director of the United States Patent and Trademark Office*

SEQUENCE LISTING

<160> NUMBER OF SEQ ID NOS: 14

<210> SEQ ID NO 1
<211> LENGTH: 951
<212> TYPE: DNA
<213> ORGANISM: Escherichia coli
<220> FEATURE:
<221> NAME/KEY: CDS
<222> LOCATION: (1)..(951)

<400> SEQUENCE: 1

```
atg cag atc ctg ttg gcc aac cca cgt ggt ttt tgt gcc ggg gta gac      48
Met Gln Ile Leu Leu Ala Asn Pro Arg Gly Phe Cys Ala Gly Val Asp
1               5                   10                  15 cgc gct atc agc att gtt gaa aac gcg ctt gcc att tac ggc gca ccg      96
Arg Ala Ile Ser Ile Val Glu Asn Ala Leu Ala Ile Tyr Gly Ala Pro
            20                  25                  30 ata tat gtc cgt cac gaa gtg gtg cat aac cgc tac gtg gtc gat agc     144
Ile Tyr Val Arg His Glu Val Val His Asn Arg Tyr Val Val Asp Ser
        35                  40                  45 ctg cgc gag cgt gga gct atc ttt att gag cag atc agc gaa gtg ccg     192
Leu Arg Glu Arg Gly Ala Ile Phe Ile Glu Gln Ile Ser Glu Val Pro
    50                  55                  60 gac ggc gcg atc ctg atc ttc tcc gca cat ggt gtt tct cag gcg gta     240
```

```
Asp Gly Ala Ile Leu Ile Phe Ser Ala His Gly Val Ser Gln Ala Val
 65                  70                  75                  80 cgt aac gaa gcg aaa agc cgt gat ttg acg gta ttc gac gcc acc tgt      288
Arg Asn Glu Ala Lys Ser Arg Asp Leu Thr Val Phe Asp Ala Thr Cys
                 85                  90                  95 ccg ctg gtg acc aaa gtg cat atg gaa gtc gcc cgc gcc agc cgt cgt      336
Pro Leu Val Thr Lys Val His Met Glu Val Ala Arg Ala Ser Arg Arg
            100                 105                 110 ggc gaa gag tct att ctc atc ggt cac gcc ggg cac ccg gaa gtg gaa      384
Gly Glu Glu Ser Ile Leu Ile Gly His Ala Gly His Pro Glu Val Glu
            115                 120                 125 ggg acg atg ggg cag tac agc aac cct gaa ggg gga atg tat ctg gtc      432
Gly Thr Met Gly Gln Tyr Ser Asn Pro Glu Gly Gly Met Tyr Leu Val
        130                 135                 140 gaa tcg cct gac gat gtg tgg aaa ctg acg gtc aaa aac gaa gag aag      480
Glu Ser Pro Asp Asp Val Trp Lys Leu Thr Val Lys Asn Glu Glu Lys
145                 150                 155                 160 ctc tcc ttt atg acc caa acc acg ctg tcg gta gat gac acg tct gat      528
Leu Ser Phe Met Thr Gln Thr Thr Leu Ser Val Asp Asp Thr Ser Asp
                165                 170                 175 gtg atc gac gcg ctg cgt aaa cgc ttc ccg aaa att gtc ggt ccg cgc      576
Val Ile Asp Ala Leu Arg Lys Arg Phe Pro Lys Ile Val Gly Pro Arg
            180                 185                 190 aaa gat gac atc tgc tac gcc acg act aac cgt cag gaa gcg gta cgc      624
Lys Asp Asp Ile Cys Tyr Ala Thr Thr Asn Arg Gln Glu Ala Val Arg
            195                 200                 205 gcc ctg gca gaa cag gcg gaa gtt gtg ttg gtg gtc ggt tcg aaa aac      672
Ala Leu Ala Glu Gln Ala Glu Val Val Leu Val Val Gly Ser Lys Asn
210                 215                 220 tcc tcc aac tcc aac cgt ctg gcg gag ctg gcc cag cgt atg ggc aaa      720
Ser Ser Asn Ser Asn Arg Leu Ala Glu Leu Ala Gln Arg Met Gly Lys
225                 230                 235                 240 cgc gcg ttt ttg att gac gat gcg aaa gat atc cag gaa gag tgg gtg      768
Arg Ala Phe Leu Ile Asp Asp Ala Lys Asp Ile Gln Glu Glu Trp Val
                245                 250                 255 aaa gag gtt aaa tgc gtc ggc gtg act gcg ggc gca tcg gct ccg gat      816
Lys Glu Val Lys Cys Val Gly Val Thr Ala Gly Ala Ser Ala Pro Asp
            260                 265                 270 att ctg gtg cag aat gtg gtg gca cgt ttg cag cag ctg ggt ggt ggt      864
Ile Leu Val Gln Asn Val Val Ala Arg Leu Gln Gln Leu Gly Gly Gly
            275                 280                 285 gaa gcc att ccg ctg gaa ggc cgt gaa gaa aat att gtt ttc gaa gtg      912
Glu Ala Ile Pro Leu Glu Gly Arg Glu Glu Asn Ile Val Phe Glu Val
        290                 295                 300 ccg aaa gag ctg cgt gtc gat att cgt gaa gtc gat taa                  951
Pro Lys Glu Leu Arg Val Asp Ile Arg Glu Val Asp
305                 310                 315

<210> SEQ ID NO 2
<211> LENGTH: 316
<212> TYPE: PRT
<213> ORGANISM: Escherichia coli

<400> SEQUENCE: 2

Met Gln Ile Leu Leu Ala Asn Pro Arg Gly Phe Cys Ala Gly Val Asp
1               5                   10                  15

Arg Ala Ile Ser Ile Val Glu Asn Ala Leu Ala Ile Tyr Gly Ala Pro
            20                  25                  30

Ile Tyr Val Arg His Glu Val Val His Asn Arg Tyr Val Val Asp Ser
        35                  40                  45
```

```
Leu Arg Glu Arg Gly Ala Ile Phe Ile Glu Gln Ile Ser Glu Val Pro
 50                  55                  60
Asp Gly Ala Ile Leu Ile Phe Ser Ala His Gly Val Ser Gln Ala Val
 65                  70                  75                  80
Arg Asn Glu Ala Lys Ser Arg Asp Leu Thr Val Phe Asp Ala Thr Cys
                 85                  90                  95
Pro Leu Val Thr Lys Val His Met Glu Val Ala Arg Ala Ser Arg Arg
                100                 105                 110
Gly Glu Glu Ser Ile Leu Ile Gly His Ala Gly His Pro Glu Val Glu
                115                 120                 125
Gly Thr Met Gly Gln Tyr Ser Asn Pro Glu Gly Gly Met Tyr Leu Val
            130                 135                 140
Glu Ser Pro Asp Asp Val Trp Lys Leu Thr Val Lys Asn Glu Glu Lys
145                 150                 155                 160
Leu Ser Phe Met Thr Gln Thr Thr Leu Ser Val Asp Asp Thr Ser Asp
                165                 170                 175
Val Ile Asp Ala Leu Arg Lys Arg Phe Pro Lys Ile Val Gly Pro Arg
                180                 185                 190
Lys Asp Asp Ile Cys Tyr Ala Thr Thr Asn Arg Gln Glu Ala Val Arg
                195                 200                 205
Ala Leu Ala Glu Gln Ala Glu Val Val Leu Val Val Gly Ser Lys Asn
                210                 215                 220
Ser Ser Asn Ser Asn Arg Leu Ala Glu Leu Ala Gln Arg Met Gly Lys
225                 230                 235                 240
Arg Ala Phe Leu Ile Asp Asp Ala Lys Asp Ile Gln Glu Glu Trp Val
                245                 250                 255
Lys Glu Val Lys Cys Val Gly Val Thr Ala Gly Ala Ser Ala Pro Asp
                260                 265                 270
Ile Leu Val Gln Asn Val Val Ala Arg Leu Gln Leu Gly Gly Gly
                275                 280                 285
Glu Ala Ile Pro Leu Glu Gly Arg Glu Glu Asn Ile Val Phe Glu Val
290                 295                 300
Pro Lys Glu Leu Arg Val Asp Ile Arg Glu Val Asp
305                 310                 315

<210> SEQ ID NO 3
<211> LENGTH: 26
<212> TYPE: DNA
<213> ORGANISM: Artificial sequence
<220> FEATURE:
<223> OTHER INFORMATION: lytB-N-out primer

<400> SEQUENCE: 3
taggatcccc ggcctagatg actgcg                                    26

<210> SEQ ID NO 4
<211> LENGTH: 42
<212> TYPE: DNA
<213> ORGANISM: Artificial sequence
<220> FEATURE:
<223> OTHER INFORMATION: ltyB-N-in primer

<400> SEQUENCE: 4
cccatccact aaacttaaac acaacaggat ctgcatgtta cg                  42

<210> SEQ ID NO 5
<211> LENGTH: 40
```

```
<212> TYPE: DNA
<213> ORGANISM: Artificial sequence
<220> FEATURE:
<223> OTHER INFORMATION: ltyB-C-in primer

<400> SEQUENCE: 5
tgtttaagtt tagtggatgg gcgtgaagtc gattagtcat                           40

<210> SEQ ID NO 6
<211> LENGTH: 27
<212> TYPE: DNA
<213> ORGANISM: Artificial sequence
<220> FEATURE:
<223> OTHER INFORMATION: ltyB-C-out primer

<400> SEQUENCE: 6
tagtcgacag aaccacccat gatcacc                                         27

<210> SEQ ID NO 7
<211> LENGTH: 36
<212> TYPE: DNA
<213> ORGANISM: Artificial sequence
<220> FEATURE:
<223> OTHER INFORMATION: Mev-kin-Sc-forward primer

<400> SEQUENCE: 7
taggaggaat taaccatgtc attaccgttc ttaact                               36

<210> SEQ ID NO 8
<211> LENGTH: 33
<212> TYPE: DNA
<213> ORGANISM: Artificial sequence
<220> FEATURE:
<223> OTHER INFORMATION: Mev-kin-Sc-reverse primer

<400> SEQUENCE: 8
ttgatctgcc tcctatgaag tccatggtaa att                                  33

<210> SEQ ID NO 9
<211> LENGTH: 42
<212> TYPE: DNA
<213> ORGANISM: Artificial sequence
<220> FEATURE:
<223> OTHER INFORMATION: Pmev-kin-Sc-forward primer

<400> SEQUENCE: 9
acttcatagg aggcagatca aatgtcagag ttgagagcct tc                        42

<210> SEQ ID NO 10
<211> LENGTH: 34
<212> TYPE: DNA
<213> ORGANISM: Artificial sequence
<220> FEATURE:
<223> OTHER INFORMATION: Pmev-kin-Sc-reverse primer

<400> SEQUENCE: 10
gagtattatc ctcctattta tcaagataag tttc                                 34

<210> SEQ ID NO 11
<211> LENGTH: 42
<212> TYPE: DNA
<213> ORGANISM: Artificial sequence
<220> FEATURE:
<223> OTHER INFORMATION: Decarb-Sc-forward primer

<400> SEQUENCE: 11
```

-continued

```
gataaatagg aggtaatact catgacccgt tacacagcat cc                    42

<210> SEQ ID NO 12
<211> LENGTH: 21
<212> TYPE: DNA
<213> ORGANISM: Artificial sequence
<220> FEATURE:
<223> OTHER INFORMATION: Decarb-Sc-reverse primer

<400> SEQUENCE: 12
ttattccttt ggtagaccag t                                           21

<210> SEQ ID NO 13
<211> LENGTH: 27
<212> TYPE: DNA
<213> ORGANISM: Artificial sequence
<220> FEATURE:
<223> OTHER INFORMATION: eclytbfor primer

<400> SEQUENCE: 13
ggatccatgc agatcctgtt ggccaac                                     27

<210> SEQ ID NO 14
<211> LENGTH: 28
<212> TYPE: DNA
<213> ORGANISM: Artificial sequence
<220> FEATURE:
<223> OTHER INFORMATION: ecltybrev primer

<400> SEQUENCE: 14
aagcttttaa tcgacttcac gaatatcg                                    28
```